United States Patent
Boman

(10) Patent No.: US 11,690,581 B2
(45) Date of Patent: Jul. 4, 2023

(54) TUMOR POSITION DETERMINATION

(71) Applicant: C-Rad Positioning AB, Uppsala (SE)

(72) Inventor: Erik Boman, Uppsala (SE)

(73) Assignee: C-RAD POSITIONING AB, Uppsala (SE)

( * ) Notice: Subject to any disclaimer, the term of this patent is extended or adjusted under 35 U.S.C. 154(b) by 368 days.

(21) Appl. No.: 17/013,738

(22) Filed: Sep. 7, 2020

(65) Prior Publication Data

US 2022/0071577 A1    Mar. 10, 2022

(51) Int. Cl.
*A61B 6/00* (2006.01)
*A61B 6/12* (2006.01)
(Continued)

(52) U.S. Cl.
CPC .............. *A61B 6/12* (2013.01); *A61B 6/0407* (2013.01); *A61B 6/08* (2013.01); *A61B 6/4085* (2013.01); *A61B 6/461* (2013.01); *G06T 7/70* (2017.01); *G06T 2207/10081* (2013.01); *G06T 2207/10088* (2013.01); *G06T 2207/20081* (2013.01); *G06T 2207/20084* (2013.01); *G06T 2207/30096* (2013.01)

(58) Field of Classification Search
CPC ........ A61N 5/1049; G06T 2207/20081; G06T 2207/10104; G06T 2207/10088; G06T 2207/10081; G06T 2207/30096
See application file for complete search history.

(56) References Cited

U.S. PATENT DOCUMENTS 9,754,371 B2    9/2017 Kateb et al.
10,201,717 B2    2/2019 Berlinger et al.
(Continued)

FOREIGN PATENT DOCUMENTS

WO    2016/097050 A1    6/2016
WO    2016/122957 A1    8/2016
WO    2020/086976 A1    4/2020

OTHER PUBLICATIONS

Bertholet et al., Real-time intrafraction motion monitoring in external beam radiotherapy, Physics in Medicine & Biology, 64: 15TR01 (Aug. 7, 2019).
(Continued)

*Primary Examiner* — Dani Fox
(74) *Attorney, Agent, or Firm* — Porter Wright Morris & Arthur LLP

(57) ABSTRACT

A computer-implemented tumor position determining model is trained, based on a plurality of sets of image data, to determine a subsequent position of a tumor in a subject based on a subsequent 2D or 3D representation of a surface of the subject, an initial image of the tumor in the subject and an initial 2D or 3D representation of a surface of the subject. Each set of image data comprises an initial training image of a tumor in a subject, an initial training 2D or 3D representation of a surface of the subject, a subsequent training image of the tumor in the subject and a subsequent training 2D or 3D representation of a surface of the subject. The subsequent training image and the subsequent training 2D or 3D representation are taken at a subsequent point in time than the initial training image and the initial training 2D or 3D representation and the plurality of sets of image data are from a plurality of different subjects.

31 Claims, 7 Drawing Sheets

(51) Int. Cl.
 A61B 6/08 (2006.01)
 A61B 6/04 (2006.01)
 G06T 7/70 (2017.01)

(56) References Cited

U.S. PATENT DOCUMENTS

| | | |
|---|---|---|
| 2014/0107390 A1 | 4/2014 | Brown et al. |
| 2016/0217595 A1* | 7/2016 | Han .................... G06T 7/74 |
| 2018/0005378 A1 | 1/2018 | Varkuti et al. |
| 2018/0247415 A1 | 8/2018 | Battle et al. |
| 2019/0220986 A1* | 7/2019 | Magro .................. A61B 6/032 |
| 2020/0069967 A1 | 3/2020 | Mori et al. |
| 2020/0129784 A1 | 4/2020 | Bériault et al. |
| 2020/0155870 A1 | 5/2020 | Takahashi et al. |
| 2020/0160972 A1 | 5/2020 | Bériault et al. |
| 2020/0234443 A1 | 7/2020 | Yan et al. |

OTHER PUBLICATIONS

Ma et al, Optical Surface Management System for Patient Positioning in Interfractional Breast Cancer Radiotherapy, BioMed Research International 2018: Article ID 6415497 (2018).

Lempart, Michael et el., Development of a novel radiotherapy motion phantom using a stepper motor driver circuit and evaluation using optical surface scanning, Australas Phys Eng Sci Med, vol. 40, pp. 717-727 (2017).

International Search Report from corresponding International Application No. PCT/SE2021/050825 dated Nov. 10, 2021.

* cited by examiner

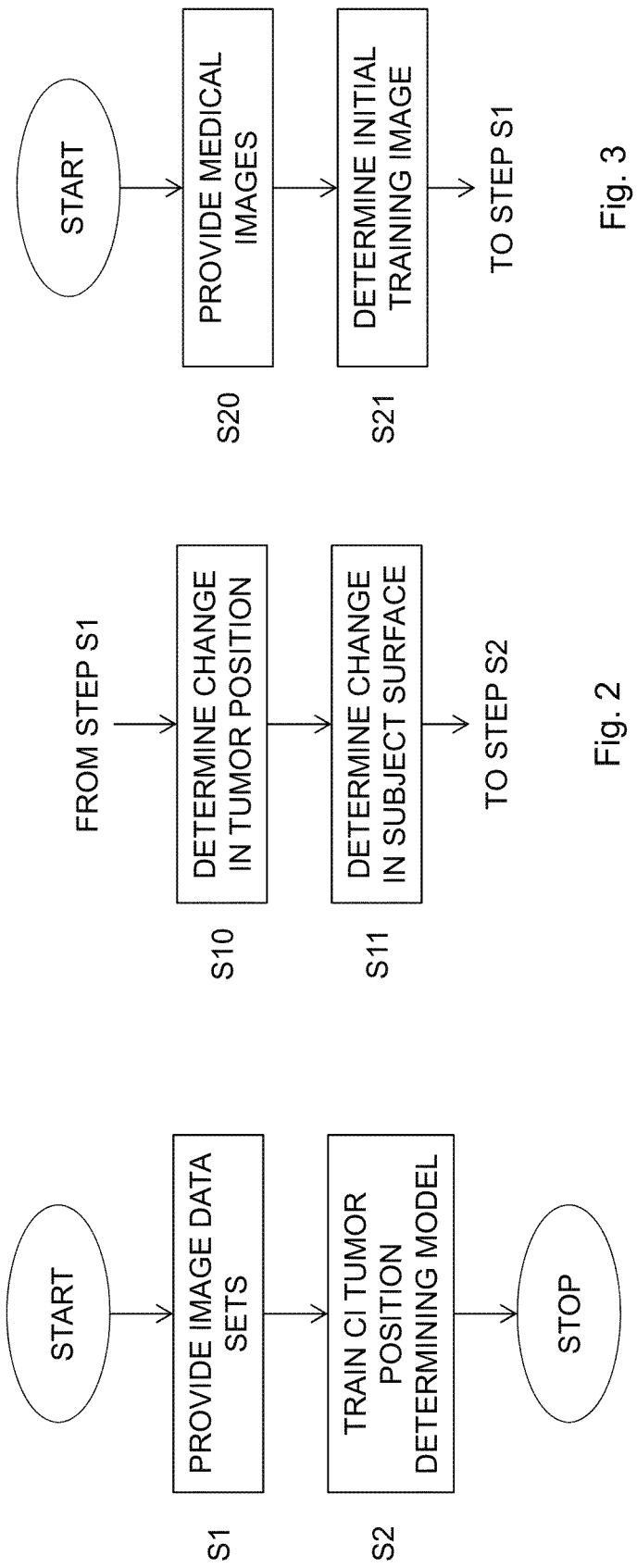

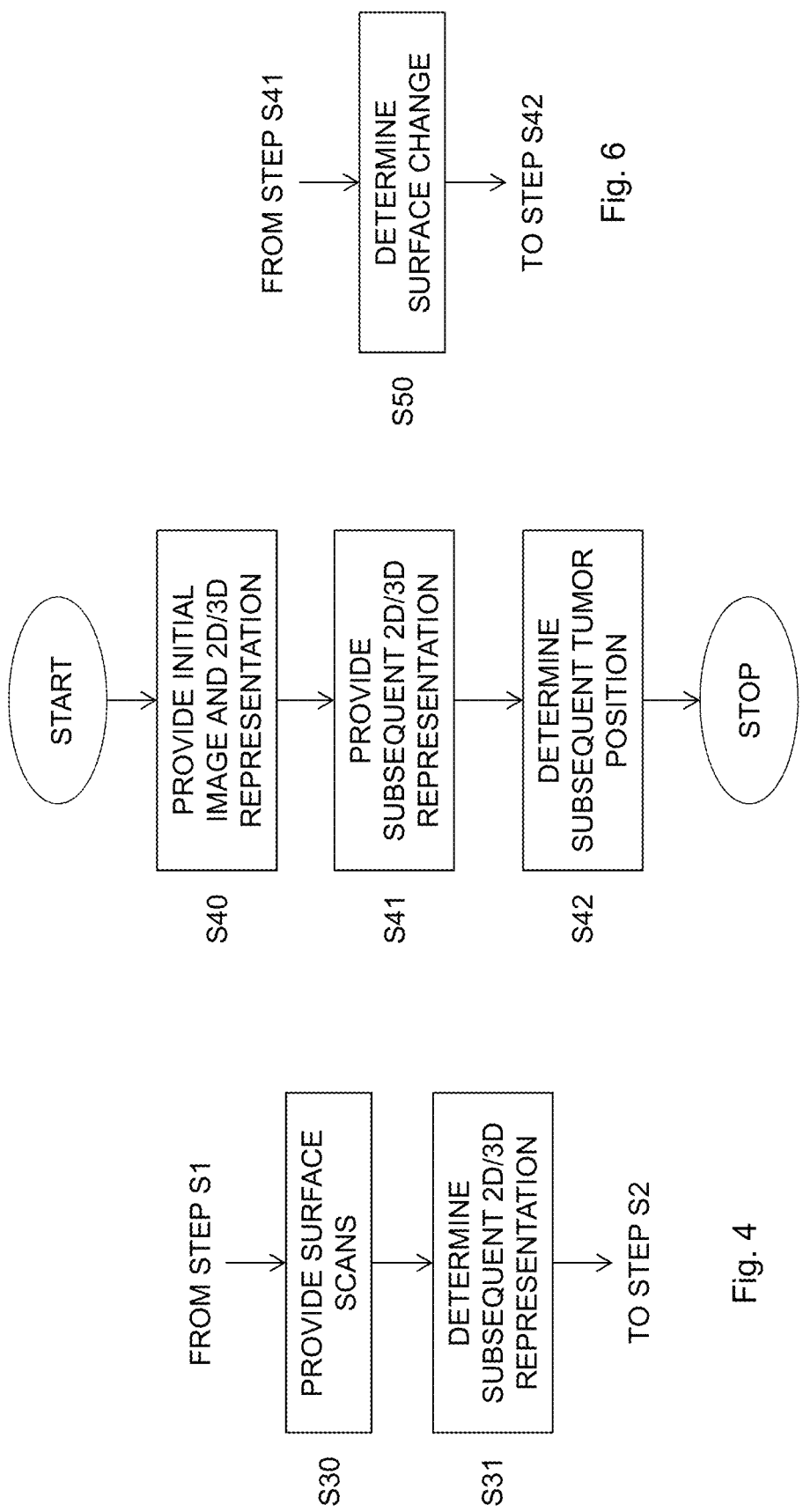

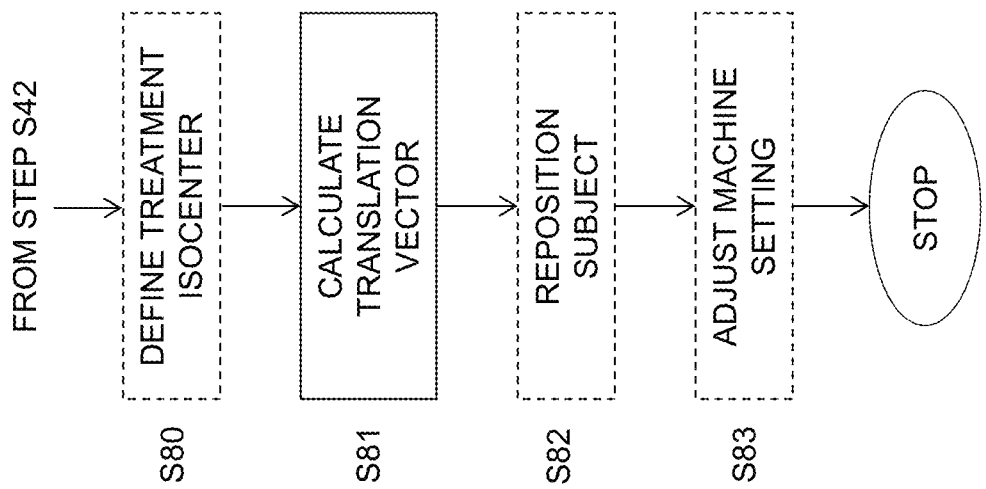
Fig. 9
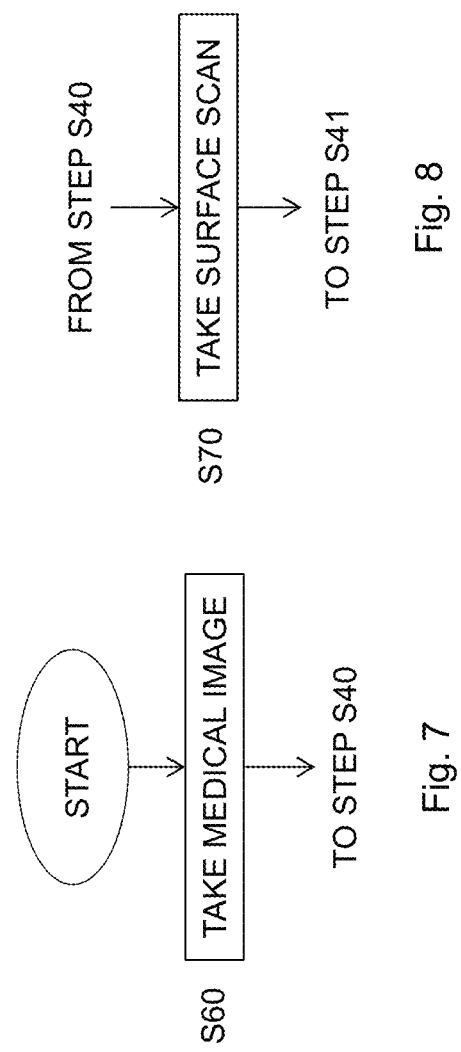
Fig. 8
Fig. 7

TUMOR POSITION DETERMINATION

TECHNICAL FIELD

The present invention generally relates to cancer diagnosis and treatment, and in particular to determining tumor position in connection with radiation therapy and medical diagnosis.

BACKGROUND

During the past decades there have been considerable developments within the fields of radiation therapy and medical diagnosis. The performance of external beam radiation therapy accelerators, brachytherapy and other specialized radiation therapy equipment has improved rapidly. Developments taking place in the quality and adaptability of radiation beams have included new targets and filters, improved accelerators, increased flexibility in beam-shaping through new applicators, collimator and scanning systems and beam compensation techniques, and improved dosimetric and geometric treatment verification methods have been introduced.

Furthermore, a number of powerful three-dimensional (3D) diagnostic techniques have been developed, ranging from computed tomography (CT), positron and single photon emission computed tomography (PET and SPECT) to ultrasound and magnetic resonance imaging and spectroscopy (MRI and MRS). Equally important is the increased knowledge of the biological effects of fractionated uniform and non-uniform dose delivery to tumors and normal tissues and new assay techniques, including the determination of effective cell doubling times and individual tissue sensitivities, allowing optimization of the dose delivery to tumors of complex shape and advanced stages.

A typical radiation therapy treatment process comprises a treatment planning process, often denoted simulation. This treatment planning process involves precisely identifying, in a radiation therapy simulator, the target volume comprising the tumor to be treated with radiation. Generally, a CT scan is taken of the region of the body to be treated. This CT scan can be used to not only precisely locate the tumor but also as a basis for determining the treatment fields and creating a map to design the radiation therapy treatment. The result of the treatment planning process is a treatment plan defining various parameters relating to the actual radiation therapy including, for instance, position information, settings of the radiation therapy machine and number of treatment sessions.

At each treatment session, the patient is then positioned on a couch in the radiation therapy machine according to the treatment plan as close as possible to the position determined during the simulation. Treatments may be delivered daily for multiple days a week for a number of weeks. At each treatment session it is important to keep track of the tumor and target volume in the patient. It is not uncommon that changes to the patient's body occur during the course of treatments, in particular if the treatment sessions run for a number of weeks. Such a change in patient body, such as due to gaining or loosing weight, may affect the position of the tumor inside the patient body.

The positions of the tumor in the patient body at the subsequent treatment sessions are typically estimated based on rigid or non-rigid models and surface scans of the patient, or based on portal images taken with the treatment machines. However, both these two techniques lack the accuracy of the CT scan in determining the position of the tumor in the patient body. A less accurate tumor position tracking in the patient body during the course of treatment sessions may lead to a less effective radiation treatment and/or unintentionally radiating non-tumor tissue in the vicinity of the tumor.

Hence, there is still a need for improvement of tumor position determination, such as in connection with radiation therapy.

SUMMARY

It is a general objective to provide a computer-implemented tumor positioning model that can be used to accurately determine the position of a tumor in subject's body.

This and other objectives are met by embodiments as disclosed herein.

An aspect of the invention relates to a computer-implemented (CI) method of generating a tumor position determining model. The method comprises providing a plurality of sets of image data. Each set of image data comprises an initial training image of a tumor in a subject, an initial training two-dimensional (2D) or three-dimensional (3D) representation of a surface of the subject, a subsequent training image of the tumor in the subject and a subsequent training 2D or 3D representation of a surface of the subject. The subsequent training image and the subsequent training 2D or 3D representation are taken at a subsequent point in time than the initial training image and the initial training 2D or 3D representation. The plurality of sets of image data is from a plurality of different subjects. The method also comprises training, based on the plurality of sets of image data, a CI tumor position determining model to determine a subsequent position of a tumor in a subject based on a subsequent 2D or 3D representation of a surface of the subject, an initial image of the tumor in the subject and an initial 2D or 3D representation of a surface of the subject.

Another aspect of the invention relates to a method of determining a position of a tumor in a subject. The method comprises providing an initial image of a tumor in a subject and an initial 2D or 3D representation of a surface of the subject. The method also comprises providing a subsequent 2D or 3D representation of a surface of the subject. The subsequent 2D or 3D representation is taken at a subsequent point in time than the initial image and the initial 2D or 3D representation. The method further comprises determining a subsequent position of the tumor in the subject based on the subsequent 2D or 3D representation, the initial 2D or 3D representation, the initial image and a CI tumor position determining model trained based on a plurality of sets of image data. Each set of image data comprises an initial training image of a tumor in a subject, an initial training 2D or 3D representation of a surface of the subject, a subsequent training image of the tumor in the subject and a subsequent training 2D or 3D representation of a surface of the subject. The subsequent training image and the subsequent training 2D or 3D representation are taken at a subsequent point in time than the initial training image and the initial training 2D or 3D representation. The plurality of sets of image data is from a plurality of different subjects.

A further aspect of the invention relates to a non-transitory computer-readable medium storing instructions that, when executed by a processor, cause the processor to train, based on a plurality of sets of image data, a CI tumor position determining model to determine a subsequent position of a tumor in a subject based on a subsequent 2D or 3D representation of a surface of the subject, an initial image of the tumor in the subject and an initial 2D or 3D representation of a surface of the subject. Each set of image data comprises an initial training image of a tumor in a subject, an initial training 2D or 3D representation of a surface of the subject, a subsequent training image of the tumor in the subject and a subsequent training 2D or 3D representation of a surface of the subject. The subsequent training image and the subsequent training 2D or 3D representation are taken at a subsequent point in time than the initial training image and the initial training 2D or 3D representation. The plurality of sets of image data is from a plurality of different subjects.

Yet another aspect of the invention relates to a non-transitory computer-readable medium storing instructions that, when executed by a processor, cause the processor to determine a subsequent position of a tumor in a subject based on a subsequent 2D or 3D representation of a surface of the subject, an initial 2D or 3D representation of a surface of the subject, an initial image of the tumor in the subject and a CI tumor position determining model trained based on a plurality of sets of image data. Each set of image data comprises an initial training image of a tumor in a subject, an initial training 2D or 3D representation of a surface of the subject, a subsequent training image of the tumor in the subject and a subsequent training 2D or 3D representation of a surface of the subject. The subsequent training image and the subsequent training 2D or 3D representation are taken at a subsequent point in time than the initial training image and the initial training 2D or 3D representation. The plurality of sets of image data is from a plurality of different subjects.

A related aspect of the invention defines a computer-readable storage medium comprising a computer program according to above.

The present invention also relates to a radiation therapy system comprising a radiation therapy machine comprising a radiation source configured to direct a radiation beam into a subject positioned on a couch. The radiation therapy system also comprises a surface scanning system comprising a light detector configured to take a surface scan of the subject positioned on the couch. The radiation therapy system further comprises at least one memory configured to store a CI tumor position determining model trained based on a plurality of sets of image data. Each set of image data comprises an initial training image of a tumor in a subject, an initial training 2D or 3D representation of a surface of the subject, a subsequent training image of the tumor in the subject and a subsequent training 2D or 3D representation of a surface of the subject. The subsequent training image and the subsequent training 2D or 3D representation are taken at a subsequent point in time than the initial training image and the initial training 2D or 3D representation. The plurality of sets of image data is from a plurality of different subjects. The at least one memory is also configured to store a medical image of the subject positioned on a couch in connection with a radiation therapy simulator. The radiation therapy system additionally comprises at least one processor configured to process the medical image and generate an initial image of a tumor in the subject and an initial 2D or 3D representation of a surface of the subject based on the medical image. The at least one processor is also configured to process the surface scan and generate a subsequent 2D or 3D representation of a surface of the subject based on the surface scan. The at least one processor is further configured to determine a subsequent position of the tumor in the subject based on the subsequent 2D or 3D representation, the initial 2D or 3D representation, the initial image and the computer-implemented tumor position determining model.

Another aspect of the invention relates to a radiation therapy system comprising a radiation therapy machine comprising a radiation source configured to direct a radiation beam into a subject positioned on a couch. The radiation therapy system also comprises a first surface scanning system comprising a light detector configured to take an initial surface scan of the subject positioned on a couch in connection with a medical imaging machine. The radiation therapy system further comprises a second surface scanning system comprising a light detector configured to take a subsequent surface scan of the subject positioned on the couch in connection with the radiation therapy machine. The radiation therapy system additionally comprises at least one memory configured to store a CI tumor position determining model trained based on a plurality of sets of image data. Each set of image data comprises an initial training image of a tumor in a subject, an initial training 2D or 3D representation of a surface of the subject, a subsequent training image of the tumor in the subject and a subsequent training 2D or 3D representation of a surface of the subject. The subsequent training image and the subsequent training 2D or 3D representation are taken at a subsequent point in time than the initial training image and the initial training 2D or 3D representation. The plurality of sets of image data is from a plurality of different subjects. The at least one memory is also configured to store an initial image of a tumor in the subject positioned on the couch in connection with the medical imaging machine. The radiation therapy system additionally comprises at least one processor configured to process the initial surface scan and generate an initial 2D or 3D representation of a surface of the subject based on the initial surface scan. The at least one processor is also configured to process the subsequent surface scan and generate a subsequent 2D or 3D representation of a surface of the subject based on the subsequent surface scan. The at least one processor is further configured to determine a subsequent position of the tumor in the subject based on the subsequent 2D or 3D representation, the initial 2D or 3D representation, the initial image and the computer-implemented tumor position determining model.

The present invention enables an accurate determination of the position of a tumor in a subject during a radiation therapy session by conducting the determination based on a previously trained CI tumor position determining model, 2D or 3D surface representations and an initial image of the tumor in the subject typically obtained during the treatment planning process. This means that the tumor position can be accurately determined even if the radiation treatment is divided into a plurality of treatment sessions extending over time, such as days or even weeks. The CI tumor position determining model can then accurately determine the position of the tumor in the subject even though the subject's body shape has changed between the treatment sessions, such as for a subject gaining or loosing weight. An increased accuracy in tumor position determination means a more effective radiation treatment and reduced risk of unintentionally radiating healthy tissue in the vicinity of the tumor.

BRIEF DESCRIPTION OF THE DRAWINGS

The invention, together with further objects and advantages thereof, may best be understood by making reference to the following description taken together with the accompanying drawings, in which:

FIG. 1 is a flow chart illustrating a computer-implemented method of generating a tumor position determining model according to an embodiment;

FIG. 2 is a flow chart illustrating additional, optional steps of the method shown in FIG. 1 according to an embodiment;

FIG. 3 is a flow chart illustrating additional, optional steps of the method shown in FIG. 1 according to another embodiment;

FIG. 4 is a flow chart illustrating additional, optional steps of the method shown in FIG. 1 according to a further embodiment;

FIG. 5 is a flow chart illustrating a method of determining a position of a tumor in a subject according to an embodiment;

FIG. 6 is a flow chart illustrating an additional, optional step of the method shown in FIG. 5 according to an embodiment;

FIG. 7 is a flow chart illustrating an additional, optional step of the method shown in FIG. 5 according to another embodiment;

FIG. 8 is a flow chart illustrating an additional, optional step of the method shown in FIG. 5 according to a further embodiment;

FIG. 9 is a flow chart illustrating additional, optional steps of the method shown in FIG. 5 according to an embodiment;

DETAILED DESCRIPTION

Figure 10:
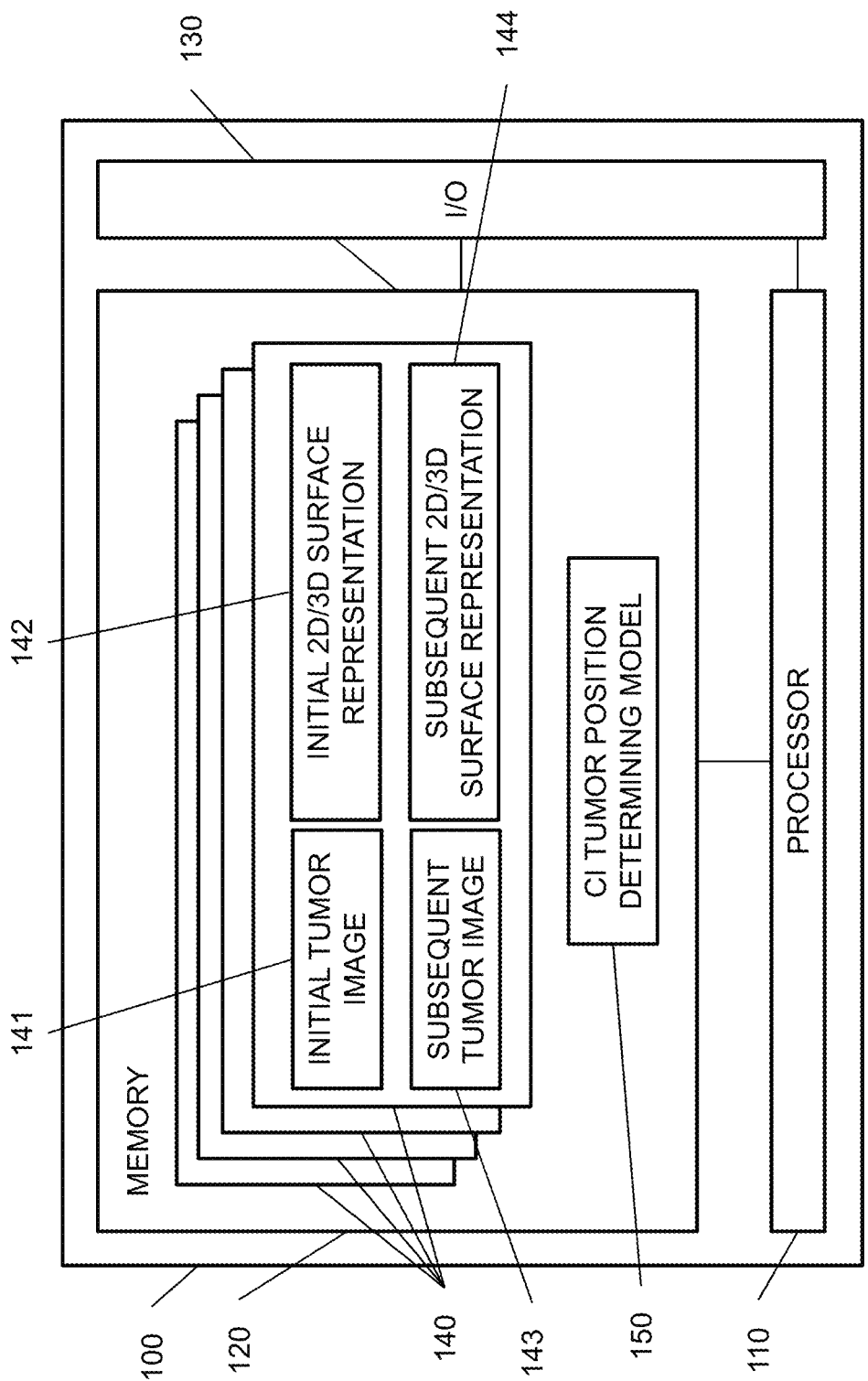
FIG. 10 is a schematic illustration of a device configured to generate a tumor position determining model.

The present invention generally relates to cancer diagnosis and treatment, and in particular to determining tumor position in connection with radiation therapy and medical diagnosis.

Today positions of the tumor in the patient body are accurately determined during the treatment planning process by using medical imaging machine(s), such as computed tomography (CT) scanners, and in particular cone beam computed tomography (CBCT) scanners, in connection with radiation therapy simulators. However, at the actual radiation therapy machine no tumor imaging is performed or tumor imaging using comparatively low quality techniques, such as portal imaging. In clear contrast, the position of the tumor in the patient body at treatment sessions in the radiation therapy machine is instead typically estimated based on rigid or non-rigid models and surface scans of the patient.

Shortcomings with these rigid and non-rigid models include non-context awareness, uniform deformability, if any, among others. Hence, the prior art rigid and non-rigid models simulate the patient body as rigid or deformable object. However, the models typically do not have any context awareness or adaption. This means that any deformation of the patient body as indicated by a change in the surface of the patient body will result in a same tumor position modification as calculated by the model regardless of whether the tumor is present adjacent to soft tissue or, for instance, bone tissue. In the former case, a deformation of the patient body will most likely induce a significant change in the tumor position in the patient body since the tumor is surrounded by deformable soft tissue. However, in the latter case, the position of the tumor will typically not move much even if the patient body has been deformed since the tumor is adjacent to or may even be connected to a bone in the patient body. This means that a change in the patient's body during the course of treatments, such as due to gaining or loosing weight, may have different effects on the tumor position in the body depending on where in the patient body the tumor is localized and the type of surrounding or adjacent tissue.

Furthermore, many prior art non-rigid models simulate the patient body with a single set of deformability and elasticity parameters although different tissues and organs will in real life be more or less deformable and movable within the patient body. A main reason for this limited representation of deformability and elasticity parameters is to reduce the complexity of the models and the estimation of the tumor position.

A less accurate tumor position tracking in the patient body during the course of treatment sessions may lead to a less effective radiation treatment. Hence, a portion of the tumor might not be effectively irradiated and thereby remain at the end of the planned treatment sessions. This may require a prolonged radiation therapy treatment process or the initial of a new radiation therapy treatment process or, if the remaining tumor is too small to be easily detected, result in tumor regrowth or recurrence in the patient.

Another problem with less accurate tumor position tracking is that non-tumor, i.e., healthy, tissue in the vicinity of the tumor may be unintentionally irradiated during the treatment sessions. This may cause damages to otherwise healthy tissue and organs with associated problems for the patient.

The present invention has taken a radically different approach by using a tumor position determining model that has been trained on training images and training two-dimensional (2D) or three-dimensional (3D) representations of patient surfaces to enable an accurate tumor position determination during the course of treatment sessions instead of or as a complement to the currently employed rigid or non-rigid models.

FIG. 1 is a flow chart illustrating a computer-implemented (CI) method of generating a tumor position determining model according to an embodiment. The method comprises providing, in step S1, a plurality of sets 140 of image data, see also FIG. 10. Each set 140 of image data comprises an initial training image 141 of a tumor in a subject, an initial training 2D or 3D representation 142 of a surface of the subject, a subsequent training image 143 of the tumor in the subject and a subsequent training 2D or 3D representation 144 of a surface of the subject. The subsequent training image 143 and the subsequent training 2D or 3D representation 144 are taken at a subsequent point in time than the initial training image 141 and the initial training 2D or 3D representation 142. According to the invention, the plurality of sets 140 of image data is from a plurality of different subjects.

The method also comprises training, in step S2 and based on the plurality of sets 140 of image data, a CI tumor position determining model 150 to determine a subsequent position of a tumor in a subject based on a subsequent 2D or 3D representation of a surface of the subject, an initial image of the tumor in the subject and an initial 2D or 3D representation of a surface of the subject.

Initial or subsequent (training) image of a tumor is also referred to as initial or subsequent (training) tumor image herein. Correspondingly, initial or subsequent (training) 2D or 3D representation of a surface is also referred to as initial or subsequent (training) 2D or 3D surface representation herein.

Hence, a CI tumor position determining model 150 is trained based on a plurality of sets 140 of image data obtained from different subjects. Each set 140 comprises an initial pair of tumor image 141 and 2D or 3D surface representation 142 and a subsequent pair of tumor image 143 and 2D or 3D surface representation 144. The initial and subsequent 2D or 3D surface representations 142, 144 represent a change in subject's body between the occasion at which the initial tumor image 141 and the initial 2D or 3D surface representation 142 were taken and the subsequent occasion at which the subsequent tumor image 143 and the subsequent 2D or 3D representation 144 were taken. Correspondingly, the initial and subsequent tumor images 141, 143 represent any change in the tumor position in the subject's body between the two occasions. The CI tumor position determining model 150 can thereby be trained to correlate changes in the subject's body with any induced change in tumor position in the subject's body based on the input sets 140 of image data.

In an embodiment, the method comprises the additional steps S10 and S11 as shown in FIG. 2. The method then continues from step S1 in FIG. 1. A next step S10 comprises determining, for each set 140 or image date, a change in tumor position in a subject based on the initial training tumor image 141 and the subsequent training tumor image 143. The method also comprises determining, in step S11 and for each set 140 of image data, a change in subject surface based on the initial training 2D or 3D surface representation 142 and the subsequent training 2D or 3D surface representation 144. The method then continues to step S2 in FIG. 2, which comprises, in this embodiment, training the CI tumor position determining model 150 based on the determined changes in tumor position and the determined changes in subject surface.

Steps S10 and S11 in FIG. 2 can be performed serially in any order or at least partly in parallel.

The CI tumor position determining model 150 can be trained to accurately determine the position of the tumor in a subject's body regardless of whether the tumor is adjacent to or surrounded by soft tissue or whether the tumor is adjacent to or even in connection with bone tissue. Thus, by providing a number of sets 140 of image data from various subjects having different positions of their tumor, the CI tumor position determining model 150 will learn how a change in subject surface affects the tumor position and any tumor deformation or movement given an initial position of the tumor in a subject's body.

This means that the CI tumor position determining model 150 can be trained to differentiate between a situation where a tumor is, for instance, positioned in deformable soft tissue from a situation where a tumor is, for instance, attached to a bone and thereby accurately determine a position of the tumor following a deformation of the subject's body and given an initial position of the tumor.

It is, though, possible to input complementary data during training of the CI tumor position determining model 150, for instance, information of the tissue type or types in vicinity of the tumor. In such an embodiment step S2 of FIG. 1 comprises training, based on the plurality of sets 140 of image date, the CI tumor position determining model 150 to determine the subsequent position of the tumor in the subject based on a change in subject surface as determined based on the initial 2D or 3D representation of a surface of the subject and the subsequent 2D or 3D representation of a surface of the subject, an initial position of the tumor and tissue type or types in vicinity of the tumor. This tissue type or types can be determined based on the initial image of the tumor in the subject.

In an embodiment, each set 140 of image data, or at least a portion thereof, comprises information of the tissue type or types in the vicinity of the tumor. For instance, the initial and/or subsequent tumor images 141, 143 may comprise tags or indications of the tissue type or types of any surrounding tissues captured in these tumor images 141, 143. In such an embodiment, the training data used to train the CI tumor position determining model 150 also comprises such information of tissue type or types.

The initial image of the tumor then also comprises image data enabling a classification of the type or types of tissue in vicinity of the tumor. For instance, the initial image may be processed by a clinician or operator that tags or marks different tissue types in the initial image. Alternatively, the initial image may be processed by a tissue classification algorithm that automatically estimates tissue type based on input image data.

The CI tumor position determining model 150 may be implemented according to various embodiments. For instance, the CI tumor position determining model 150 could be in the form a machine learning (ML) model. Generally, ML algorithms build a mathematical model based on training data, i.e., the plurality of sets 140 of image data, in order to make predictions or decisions without being explicitly programmed to do so. There are various types of ML algorithms that differ in their approach, the type of data they input and output, and the type of task or problem that they are intended to solve. Illustrative, but non-limiting, examples of such ML algorithms include supervised learning algorithms, unsupervised learning algorithms, semi-supervised learning algorithms, reinforcement learning algorithms, self-learning algorithms, feature learning algorithms, sparse dictionary learning algorithms, anomaly detection algorithms, and association rule learning algorithms.

Performing machine learning involves creating a model, which is trained on training data and can then process additional data to make predictions or decisions. Various types of ML models could be used according to the embodiments, including, but not-limited to artificial neural networks, decision trees, support vector machines, regression analysis, Bayesian networks and Genetic algorithms.

Furthermore, deep learning, also known as deep structured learning, is a ML method based on artificial neural networks with representation learning. Learning can be supervised, semi-supervised or unsupervised. Deep learning architectures, such as deep neural networks, deep belief networks, recurrent neural networks and convolutional neural networks, could be used to train and implement the CI tumor position determining model. "Deep" in deep learning comes from the use of multiple layers in the network. Deep learning is concerned with an unbounded number of layers of bounded size, which permits practical application and optimized implementation, while retaining theoretical universality under mild conditions. In deep learning the layers are also permitted to be heterogeneous and to deviate widely from biologically informed connectionist models, for the sake of efficiency, trainability and understandability.

Hence, in an embodiment, step S2 in FIG. 1 comprises training, based on the plurality of sets 140 of image data, a CI tumor position determining ML model, such as a CI tumor determining deep learning model, to determine a subsequent position of a tumor in a subject based on a subsequent 2D or 3D representation of a surface of the subject, an initial image of the tumor in the subject and an initial 2D or 3D representation of a surface of the subject.

In an embodiment, the initial training 3D surface representation 142 is a 2D or 3D representation of a surface of the subject taken in connection with the initial training tumor image 141. Correspondingly, the subsequent training 3D surface representation 144 is, in this embodiment, a 2D or 3D representation of a surface of the subject taken in connection with the subsequent training tumor image 143 in the subject.

Hence, in a preferred embodiment, the initial training 2D or 3D surface representation 142 is preferably a representation of a surface of the subject at the time of taking the initial training tumor image 141, whereas the subsequent training 2D or 3D surface representation 144 is preferably a representation of a surface of the subject at the time of taking the subsequent training tumor image 143.

As mentioned in the foregoing, the subsequent training tumor image 143 and the subsequent training 2D or 3D surface representation 144 are taken at a subsequent point in time than the initial training tumor image 141 and the initial training 2D or 3D surface representation 142. In a particular embodiment, the subsequent training tumor image 143 and the subsequent training 2D or 3D surface representation 144 are taken at least multiple, i.e., at least two, days after the initial training tumor image 141 of the tumor is taken.

For instance, the initial training tumor image 141 could be a medical image of the tumor taken in connection with a treatment planning or simulation process. The subsequent training tumor image 143 and the subsequent training 2D or 3D surface representation 144 could then be taken at a subsequent point in time, such as at a point during radiation treatment, for instance in connection with a treatment session, or any point in time after the radiation treatment, for instance in connection with a follow-up occasion.

Having a period of time of at least multiple days between taking the initial and subsequent training tumor images 141, 143 implies that the chances of changes in the subjects' bodies are higher as compared to taking these training tumor images 141, 143 at substantially the same period of time. The different sets 140 of image data may, though, have the same or different periods of time between taking the initial and subsequent training tumor images 141, 143.

FIG. 3 is a flow chart illustrating additional steps of the method shown in FIG. 1 according to an embodiment. In this embodiment, medical images of subjects are provided in step S20. A next step S21 comprises determining, from each medical image of a subject, an initial training image 141 of a tumor in the subject and an initial training 2D or 3D representation 142 of a surface of the subject. The method then continues to step S1 in FIG. 1.

Hence, medical images of subjects could be used to determine not only the initial training tumor images 141 but also the initial training 2D or 3D surface representations 142. The medical images thereby also comprise surface structures or image data enabling creation or estimation of such surface structures. Examples of medical images that could be used to determine not only the initial training tumor images 141 but also the initial training 2D or 3D surface representations 142 include CT images, such as CBCT images, magnetic resonance imaging (MRI) images and positron emission tomography (PET)/CT images.

In a particular embodiment, step S20 of FIG. 3 comprises providing CBCT images of subjects. In this particular embodiment, step S21 comprises determining, from each CBCT image of a subject, an initial training image of a tumor in the subject and an initial training 3D representation of a surface of the subject.

CBCT scanning is traditionally used as a part of the treatment planning process. In such a case, a CBCT scan is taken of the region of the body to be treated to precisely locate the tumor and the treatment fields and create a map to design the radiation therapy treatment. The CBCT scan can then be used to create both the initial training tumor image 141 and the initial training 3D surface representation 142.

An advantage of the present invention is that image data taken with different image modalities or techniques, and thereby using different types of medical imaging machines, could be used to train the CI tumor position determining model 150. Hence, the invention is not limited to using a single type of medical images but could use various types of medical images as training data for the CI tumor position determining model 150. The amount of training data that could be used to train the CI tumor position determining model 150 can be significantly increased when using tumor images obtained from different imaging modalities. This will in turn increase the accuracy in tumor position determination of the CI tumor position determining model but also enables the CI tumor position determining model to determine subsequent tumor positions in subjects even though the input initial tumor images are obtained using different types of medical imaging machines.

In an embodiment, the plurality of sets 140 of image data comprises images of tumors in subjects as taken with different image modalities. In a particular embodiment, the different image modalities are selected from the group consisting of CT, PET, PET/CT, ultrasound and MRI. This means that the CI tumor position determining model can be trained using a combination of CT images, PET images, PET/CT images, ultrasound images and/or MRI images. In various embodiments, the CI tumor position determining model is trained using a combination of CT images and PET images, a combination of CT images and PET/CT images, a combination of CT images and ultrasound images, a combination of CT images and MRI images, a combination of CT images, PET images and PET/CT images, a combination of CT images, PET images and ultrasound images, a combination of CT images, PET images and MRI images, a combination of CT images, PET/CT images and ultrasound images, a combination of CT images, PET/CT images and MRI images, a combination of CT images ultrasound images and MRI images, a combination of CT images, PET images, PET/CT images and ultrasound images, a combination of CT images, PET images, PET/CT images and MRI images, a combination of CT images, PET/CT images, ultrasound images and MRI images, a combination of CT images, PET images, ultrasound images and MRI images, a combination of CT images, PET images, PET/CT images and MRI images or a combination of CT images, PET images, PET/CT images, ultrasound images and MRI images. CT images also include CBCT images.

In an embodiment, the subsequent training tumor images 143 and the subsequent training 2D or 3D surface representations 144 could also be derived or determined from medical images as the initial training tumor images 141 and the initial training 2D or 3D surface representations 142 as described above. In another embodiment, a surface scanning system is used to generate surface scans of subjects and the subsequent training 2D or 3D surface representations 144 could then be determined from such surface scans. The surface scanning system may then be arranged or disposed at or in connection with medical imaging machines used to generate the subsequent training tumor images 143.

The initial and subsequent training 2D and 3D surface representations 142, 144 may be 2D surface representations or 3D surface representations. In an embodiment, both the initial and subsequent training surface representations 142, 144 are 2D surface representations. In another, currently preferred, embodiment, both the initial and subsequent training surface representations 142, 144 are 3D surface representations.

2D surface representations could be surface representations of fiducials or markers in the skin of the subject, natural fiducials of the subject, such as nipple or belly button, and/or fiducials positioned and optionally attached or anchored to the subject's body. Another example of 2D surface representation is a scanned line along at least a portion of the surface of the subject's body, such as along a longitudinal (cephalic-caudal) axis or along a sagittal axis.

In a currently preferred embodiment, the initial and subsequent training surface representations 142, 144 are 3D surface representations of at least a portion of the subject's body. Generally, a more accurate matching and alignment of surface representations can be made if the surface representations are 3D surface representations.

It is possible that at least portion of the initial training surface representations 142 are 2D surface representations and the remaining initial training surface representations 142 are 3D surface representations and/or at least portion of the subsequent training surface representations 144 are 2D surface representations and the remaining subsequent training surface representations 144 are 3D surface representations.

FIG. 4 is a flow chart illustrating additional steps of the method shown in FIG. 1. The method continues from step S1 in FIG. 1. A next step S30 comprises providing surface scans of subjects taken by a surface scanning system comprising a light detector in connection with taking the subsequent training images. This embodiment also comprises determining, in step S31 and from each surface scan, a subsequent 2D or 3D representation of a surface of a subject. The method then continues to step S2 in FIG. 1.

The surface scanning system comprises at least one light detector configured to detect light from the surface of the subject. The detector may be configured to detect ultraviolet (UV) light, visible light and/or infrared (IR) light. A currently preferred example is to have a light detector configured to detect at least visible light or at least a portion of the spectrum of visible light. Although, a light detector configured to detect UV light, visible light and/or IR light is a preferred implementation the embodiments are not limited thereto. Hence, the light detector could instead, or alternatively, be configured to detect other forms of electromagnetic radiation.

In an embodiment, the surface scanning system comprises at least one light source or projector configured to project light onto the subject. The at least one light projector may, for instance, be at least one UV light projector, at least one visible light projector and/or at least one IR light projector, preferably at least one visible light projector.

The light projector could project a general light beam or dot that is moved over the subject's body, a structured light or a light pattern.

It is generally preferred to include at least one light projector in the surface scanning system. However, the at least one light projector may be omitted in cases where the treatment (planning) room comprises an ambient light source. For instance, a light detector could be used to detect ambient light reflected from the subject's body surface and where this ambient light comes from one or more light sources, such as lamps, in the treatment (planning) room and/or from one or more windows.

Examples of surface scanning systems that could be used according to the embodiments include Catalyst, Catalyst HD, Catalyst, Catalyst HD and Catalyst Tomo from C-RAD Positioning AB. The embodiments are, however, not limited thereto but could use any surface scanning system capable of determining a 2D or 3D representation of at least a portion of a surface of a subject including, for instance, optical surface monitoring system (OSMS), Calypso® or IDENTIFY™ by Varian, GateRT® (Advance) or AlignRT® Advance by Vision RT or ExacTrac Dynamic by Brainlab.

Surface scans of subjects determined using a surface scanning system as disclosed above could also, or alternatively, be used to determine the initial 2D or 3D surface representation 142. In such a case, the surface scan system is preferably arranged or disposed at or in connection with medical imaging machines used to generate the initial training tumor images 141.

A single CI position determining model could be trained according to the embodiments and subsequently used for determining a position of a tumor in a subject as will be further described herein regardless of the general position of the tumor in the body. It is, however, possible to train and use multiple CI position determining models that are adapted to different portions of the body, such as one model if the tumor is in the torso and another model if the tumor is in the head or skull. It is also possible to use more than two different models to, for instance, handle tumors in limbs (arms and legs) and/or have different models for the chest part of the torso and the abdominal part of the torso.

The CI tumor position determining model can be generated according to the embodiments and as discussed above in connection with FIGS. 1 to 4. In such an embodiment, the CI tumor position determining model is created by training using the plurality of sets of image data. The method as shown in FIG. 1 can also be used to update an existing CI tumor position determining model by training it further using image data. Hence, an already existing CI tumor position determining model can be further trained and updated as new image data is available to thereby even further improve the accuracy of the CI tumor position determining model. For instance, the CI position determining model could be used for determining a position of a tumor in a subject as will be described further herein in connection with FIG. 5. It may also be possible, for such a patient, to get an accurate verification of the actual position of the tumor in the subject, such as using CT images, MRI images and/or PET/CT images. In such a case, the CI tumor position determining model could be trained based on any difference in predicted position of the tumor and the actual position of the tumor. Alternatively, or in addition, the outcome of the radiation treatment could be used as an input to further train the CI tumor position determining model, i.e., whether the predicted position of the tumor in the subject was sufficient accurate to lead to an efficient eradication of the tumor with low radiation doses to adjacent healthy tissue or whether at least part of the tumor remains after the planned radiation treatment sessions.

Such a computer-implemented method of updating a tumor position determining model may comprise providing at least one set of image data, each set of image data comprises an initial image of a tumor in a subject, an initial 2D or 3D representation of a surface of the subject, a subsequent image of the tumor in the subject and a subject 2D or 3D representation of a surface of the subject. The subsequent image and the subsequent 2D or 3D representation are taken at a subsequent point in time than the initial image and the initial 2D or 3D representation. The method also comprises updating, based on the at least one set of image data, a computer-implemented tumor position determining model to determine a subsequent position of a tumor in a subject based on a subsequent 2D or 3D representation of a surface of the subject, an initial image of the tumor in the subject and an initial 2D or 3D representation of a surface of the subject.

In another embodiment, the set of image data used to update the CI tumor position determining model comprises the initial and subsequent 2D or 3D surface representations and difference data representing a difference in tumor position in a subject between a predicted position of the tumor as determined by the CI tumor position determining model and an actual position of the tumor, such as determined using medical imaging of the subject.

In a further embodiment, the set of image data used to update the CI tumor position determining model comprises the initial and subsequent 2D or 3D surface representations and information of the outcome of a scheduled radiation treatment for the subject. The information may, for instance, be in the form of successful treatment, i.e., eradication of the tumor, versus unsuccessful treatment, i.e., at least part of the tumor remaining following the scheduled radiation treatment. It is also possible to have more quantitative information, such as a percentage of the tumor volume remaining after the scheduled radiation treatment.

FIG. 10 is a schematic illustration of a device 100 configured to generate a CI tumor position determining model 150 according to an embodiment. The device 100 comprises a memory 120 configured to, at least temporarily, store sets 140 of image data comprising initial and subsequent training tumor images 141, 143 and initial and subsequent training 2D or 3D surface representations 142, 144. The memory 120 also comprises the trained CI tumor position determining model 150. The device 100 in FIG. 10 has been shown with a single memory 120. The embodiments are, however, not limited thereto. In clear contrast, the device 100 could comprise or be, wirelessly or with wire, connected to multiple memories 120, such as memory system of multiple memories. The device 100 also comprises a processor 110 configured to process received input image data and train the CI tumor position determining model 150 based on the image data. The device 100 further comprises a general input and output (I/O) unit 130 configured to communicate with external devices. The I/O unit 130 could represent a transmitter and receiver, or transceiver, configured to conduct wireless communication. Alternatively, or in addition, the I/O unit 130 could be configured to conduct wired communication and may then, for instance, comprise one or more input and/or output ports.

FIG. 5 is a flow chart illustrating a method of determining a position of a tumor in a subject. The method comprises providing, in step S40, an initial image of a tumor in a subject and an initial 2D or 3D representation of a surface of the subject. The method also comprises providing, in step S41, a subsequent 2D or 3D representation of a surface of the subject. The subsequent 2D or 3D representation is taken at a subsequent point in time than the initial image and the initial 2D or 3D representation. The method further comprises determining, in step S42, a subsequent position of the tumor in the subject based on the subsequent 2D or 3D representation, the initial 2D or 3D representation, the initial image and CI tumor position determining model. The CI tumor position determining model is trained based on a plurality of sets 140 of image data, each set 140 of image data comprises an initial training image 141 of a tumor in a subject, an initial training 2D or 3D representation 142 of a surface of the subject, a subsequent training image 143 of the tumor in the subject and a subsequent training 2D or 3D representation 144 of a surface of the subject. The subsequent training image 143 and the subsequent training 2D or 3D representation 144 are taken at a subsequent point in time than the initial training image 141 and the initial training 2D or 3D representation 142. According to the invention, the plurality of sets 140 of image data is from a plurality of different subjects.

The method as shown in FIG. 5, thus, defines the use of the CI position determining model to determine the position of a tumor in a subject at a subsequent point in time based on information of an initial position of the tumor in the subject's body, i.e., the initial tumor image of the tumor, and based on the initial and subsequent 2D or 3D surface representations. Hence, the CI position determining model can determine the subsequent or changed position of the tumor in the subject's body given an initial position of the tumor and surface representations of at least a portion of the subject. The 2D or 3D surface representations then represent a change or deformation in the subject's body between the point in time when the initial image of the tumor and the initial 2D or 3D surface representation were taken and the point in time when the subsequent 2D or 3D surface representation was taken. The CI position determining model can then model or correlate such a change or deformation in the subject's body into any change or deformation in the position of the tumor and can thereby be used to determine the position of the tumor in the subject's body at the point in time when the subsequent 3D surface representation was taken.

In an embodiment, the method comprises an additional step S50 as shown in FIG. 6. In such a case, the method continues from step S41 in FIG. 5. The next step S50 comprises determining a change in subject surface based on the initial 2D or 3D representation and the subsequent 2D or 3D representation. The method then continues to step S42 in FIG. 5, which, in this embodiment, comprises determining the subsequent position of the tumor in the subject based on the change in subject surface, the initial image and the CI tumor position determining model.

As discussed in the foregoing, also information of tissue type or types in vicinity of the tumor could be used by the CI tumor position determining model when determining the position of the tumor. In such a case, step S42 in FIG. 5 comprises determining the subsequent position of the tumor in the subject based on a change in subject surface as determined based on the initial 2D or 3D surface representation and the subsequent 2D or 3D surface representation, an initial position of the tumor and tissue type or types in vicinity of the tumor and the CI tumor position determining model. In a particular embodiment, the tissue type or types is or are determined based on the initial image.

The initial tumor image then also comprises image data enabling a classification of the type or types of tissue in vicinity of the tumor. For instance, the initial tumor image may be processed by a clinician or operator that tags or marks different tissue types in the initial image. Alternatively, the initial tumor image may be processed by a tissue classification algorithm that automatically estimates tissue type based on input image data.

FIG. 7 is a flow chart illustrating an additional step of the method in FIG. 5 according to an embodiment. This embodiment comprises taking, in step S60, a medical image of the subject. The method then continues to step S40 in FIG. 5. In this embodiment, step S40 comprises generating the initial image of the tumor in the subject and the initial 2D or 3D representation of a surface of the subject based on the medical image.

As mentioned in the foregoing, images of the tumor taken using selected imaging modalities or techniques, such as CT, MRI and PET/CT, could be used to derive not only the initial tumor image but also a surface representation of at least a portion of the subject's body, i.e., the initial 2D or 3D surface representation. Hence, in an embodiment, the medical image is selected from the group consisting of a CT image, a MRI image and a PET/CT image.

Figure 11:
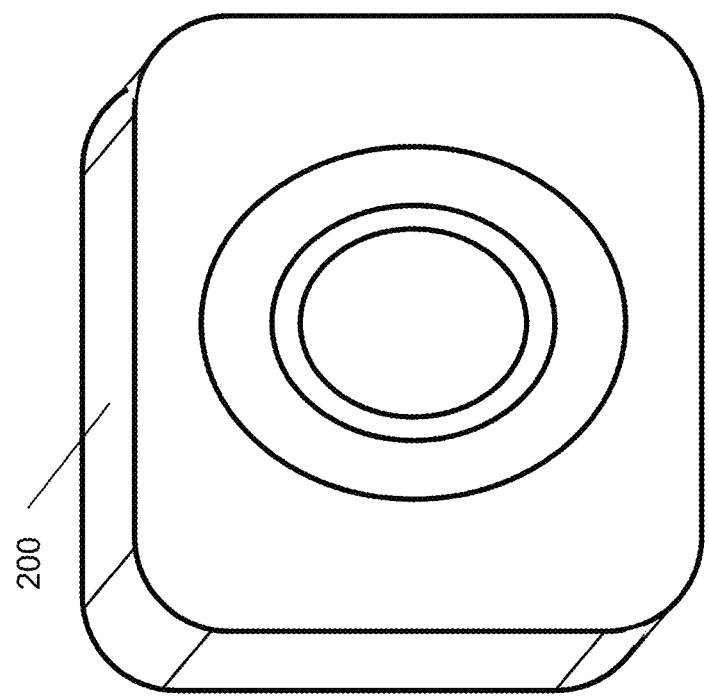
FIG. 11 is a schematic illustration of a medical imaging machine.

In an embodiment, step S60 comprises taking the medical image of the subject using a medical imaging system 200 arranged at or in connection with a radiation therapy simulator, see FIG. 11. Hence, the medical image used to derive the initial image of the tumor and the initial 2D or 3D surface representation is preferably taken as a part of the treatment planning or simulation process. For instance, the medical image could be a CBCT image of at least a portion of the subject taken using a CBCT scanner 200 employed as a part of the treatment planning process. FIG. 11 schematically illustrates a medical imaging machine, such as a CBCT scanner 200 used to take CBCT images that could be used as a basis for determining initial tumor images and initial 2D or 3D surface representations.

FIG. 8 is a flow chart illustrating an additional step of the method in FIG. 5 according to an embodiment. The method continues from step S40 in FIG. 5. A next step S70 comprises taking a surface scan of the subject using a light detector. The method then continues to step S41, which, in this embodiment, comprises generating the subsequent 3D representation of a surface of the subject based on the surface scan.

Figure 12:
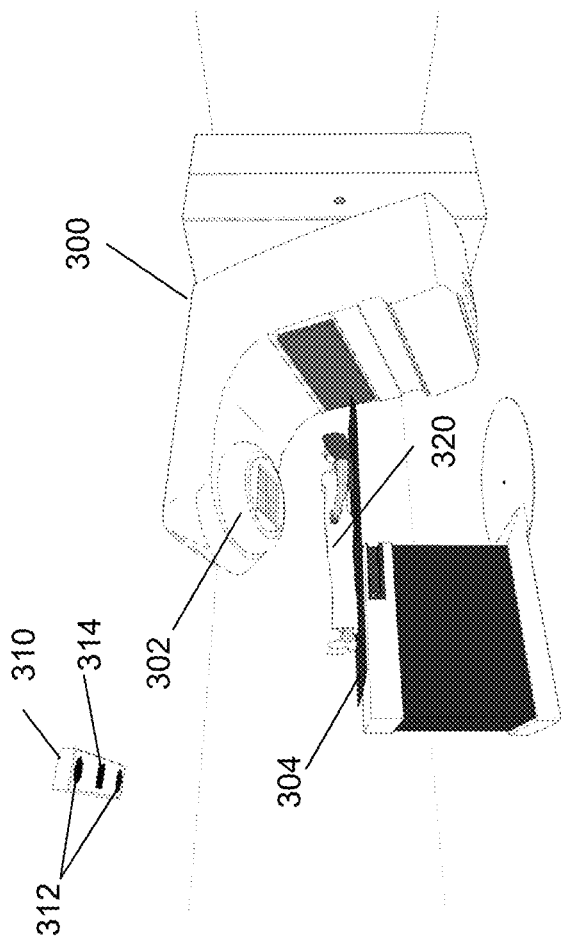
FIG. 12 is a schematic illustration of a radiation therapy machine and a surface scanning system.

In a particular embodiment, step S70 comprises taking the surface scan of the subject using a light detector 312 and optionally, but preferably, a light projector 314 arranged at or in connection with a radiation therapy machine 300. FIG. 12 schematically illustrates a radiation therapy machine 300 configured to irradiate a tumor (target volume) in a subject 320 positioned on a couch or table 304. The figure also illustrates a surface scanning system 300 comprising at least one light projector 314 and at least one light detector 312. The surface scanning system 300 can then be used to take a surface scan of at least a portion of the subject 320 positioned on the couch 304 and this surface scan is used to determine the subsequent 2D or 3D surface representation.

A surface scanning system may also, or alternatively, be arranged in connection with a medical imaging machine used to determine the initial tumor image. In such a case, the surface scan from such a surface scanning system could be used to determine the initial 2D or 3D surface representation. For instance, a first surface scanning system could be arranged at or in connection with the medical imaging machine and a second surface scanning system could be arranged at or in connection with the radiation therapy machine.

The discussion in the foregoing relating to the usage of 2D surface representations and/or 3D surface representations for the initial and subsequent training surface representations also apply to the initial and subsequent 2D or 3D surface representation.

The initial position of the tumor is defined based on the initial tumor image. This initial tumor image could, for instance, be manually processed by a clinician or operator in order to identify the tumor in the initial tumor image. Alternatively, or in addition, a tumor identification algorithm could process the initial tumor image in order to identify the tumor in the initial tumor image.

Generally, radiation therapy machines, medical imaging machines and surface scanning systems may be associated with a respective coordinate system. For instance, the position of a tumor in a tumor image taken by a medical imaging machine could be defined in the coordinate system associated with the medical imaging machine. Correspondingly, a target volume to be irradiated in a subject positioned on a couch in connection with a radiation therapy machine is typically defined in the coordinate system associated with the radiation therapy machine. Furthermore, 2D or 3D surface representations of subjects as acquired using a surface scanning system may be defined in the coordinate system associated with the surface scanning system.

Coordinate system transformations may be used to map or transform coordinates in one coordinate system into corresponding coordinates in another coordinate system. Such coordinate system transformations may be used to provide the tumor positions in the initial and subsequent (training) tumor images and the subject surfaces in the initial and subsequent (training) 2D or 3D surface representations in a same or common coordinate system. Such coordinate system transformations involve translational shifts and rotations along axis of the coordinate system.

Hence, in a preferred embodiment, the training data used to train the CI tumor position determining model, i.e., the sets of image data, is preferably in a common coordinate system. For instance, if a surface scanning system is used in connection with medical imaging machines and radiation therapy machines, the coordinate system of the surface scanning systems could be used as a common reference.

In an embodiment, the tumor position as determined by the CI tumor position determining model based on the initial tumor image and the initial and subsequent 2D or 3D surface representations is converted from a first coordinate system associated with the CI tumor position determining model into a second coordinate system, such as a coordinate system associated with the radiation therapy machine or a coordinate system associated with a surface scanning system arranged at or in connection with the radiation therapy machine.

As mentioned in the foregoing, multiple CI tumor position determining models could be trained to be adapted to the particular portion in the subject's body where the tumor is, such as one CI tumor position determining model for a tumor somewhere in the torso and one CI tumor position determining model for a tumor in the head or skull. In such an embodiment, the method also comprises selecting a CI tumor position determining model based on the initial position of the tumor, such as represented by the initial tumor image.

FIG. 9 is a flow chart illustrating additional steps of the method in FIG. 5 according to various embodiments. In an embodiment, the method comprises calculating, in step S81, a translation vector based on the determined subsequent position of the tumor in the subject and a target position of tumor in the subject. This translation vector thereby represents a difference between a target position of the tumor in the subject and the subsequent position of the tumor as determined by the CI tumor position determining model.

In an embodiment, the method also comprises step S80 as shown in FIG. 9. This step S80 comprises defining a treatment isocenter based on the determined subsequent position of the tumor in the subject. In this embodiment, step S81 comprises calculating the translation vector based on the defined treatment isocenter and an isocenter of a radiation therapy machine 300.

The isocenter of the radiation therapy machine 300 is the point in space where radiation beams from the radiation therapy machine 300 intersect when the gantry of the radiation machine 300 is rotated. Correspondingly, treatment isocenter is the current point in the subject's body occupied by the tumor. In an ideal situation, the treatment isocenter and the isocenter of the radiation therapy machine 300 are the same or at least overlap. However, due to deformation and/or movement of the subject's body, the tumor may move inside the body so that the treatment isocenter is no longer overlapping with the isocenter of the radiation therapy machine 300. In such a case, the tumor is not efficiently targeted during the treatment session and the radiation beam may instead at least partly target adjacent healthy issue.

In an embodiment shown in FIG. 9, the treatment isocenter is determined based on the subsequent position of the tumor in the subject, which is in turn determined by the CI tumor position determining model using the initial tumor image of the tumor and the initial and subsequent 2D or 3D surface representations. The translation vector then represents the difference between treatment isocenter and the isocenter of the radiation therapy machine 300.

In an embodiment, the method comprises an additional step S82 as shown in FIG. 9. This step S82 comprises repositioning the subject 320 relative to a radiation therapy machine 300 based on the calculated translation vector. Thus, the translation vector could be used to reposition the subject 320 on the couch 304 to thereby minimize the translation vector and thereby align the treatment isocenter with the isocenter of the radiation therapy machine 300. If the subject 320 is repositioned to align the isocenters, the radiation beams from the radiation therapy machine 300 will correctly target the tumor in the subject's body. Hence, an accurate radiation therapy is achieved while minimizing radiation doses to surrounding healthy tissue.

Instead of, or as a complement to repositioning the subject 320, the method could comprise adjusting, in step S83, at least one setting of a radiation therapy machine 300 based on the calculated translation vector. In this embodiment, at least one setting of the radiation therapy machine 300 is adjusted to adapt the radiation therapy session based on the subsequent position of the tumor as determined by the CI tumor position determining model and thereby based on the non-zero translation vector. For instance, the treatment plan may be adapted to adjust the radiation therapy based on the changed position of the tumor in the subject's body and caused by a change or movement of the subject's body.

The CI tumor position determining model used in the embodiments described above in connection with FIGS. 5 to 9 is preferably generated according to any of the embodiments described above in connection with FIGS. 1 to 4.

Figure 13:
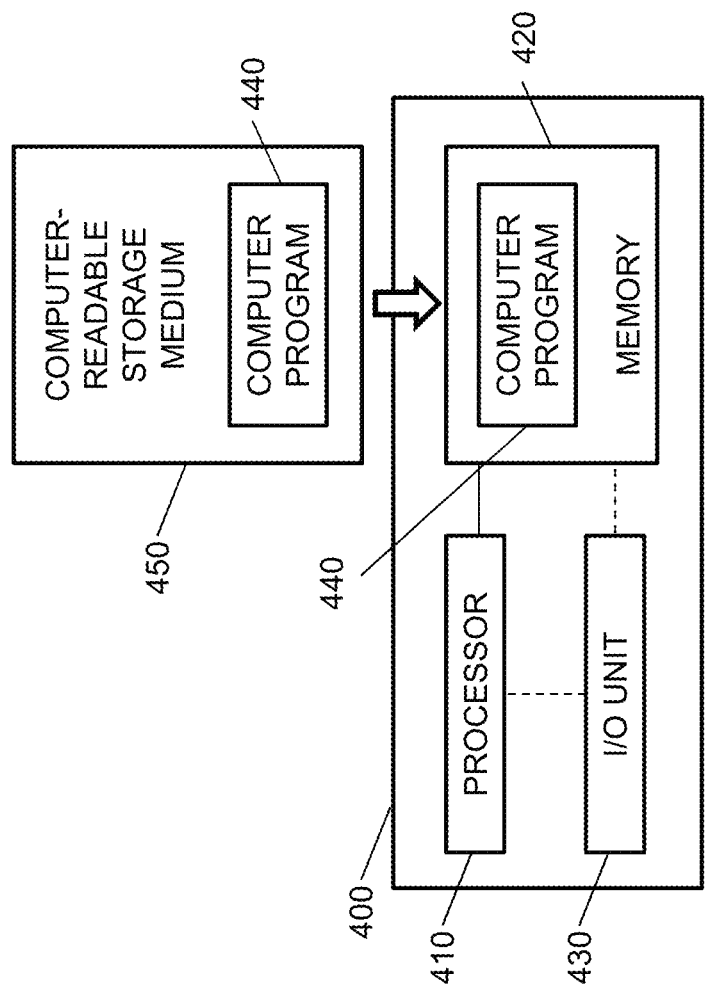
FIG. 13 is a schematic illustration of a device configured to generate a tumor position determining model and/or determine a position of a tumor in a subject according to an embodiment.

FIG. 13 is a schematic block diagram of a device 400, such as computer, comprising a processor 410 and a memory 420 that can be used to train a CI tumor position determining model and/or determine a subsequent position of a tumor using such a CI tumor position determining model. In such an embodiment, the training and/or determination could be implemented in a computer program 440, which is loaded into the memory 420 for execution by processing circuitry including one or more processors 410 of the device 400. The processor 410 and the memory 420 are interconnected to each other to enable normal software execution. An I/O unit 430 is preferably connected to the processor 410 and/or the memory 420 to enable reception of image data.

The term processor should be interpreted in a general sense as any circuitry, system or device capable of executing program code or computer program instructions to perform a particular processing, determining or computing task. The processing circuitry including one or more processors 410 is, thus, configured to perform, when executing the computer program 440, well-defined processing tasks such as those described herein.

The processor 410 does not have to be dedicated to only execute the above-described steps, functions, procedure and/or blocks, but may also execute other tasks.

In a particular embodiment, the computer program 440 comprises instructions, which when executed by a processor 410, cause the processor 410 to train, based on a plurality of sets of image data, a CI tumor position determining model to determine a subsequent position of a tumor in a subject based on a subsequent 2D or 3D representation of a surface of the subject, an initial image of the tumor in the subject and an initial 2D or 3D representation of a surface of the subject. Each set of image data comprises an initial training image of a tumor in a subject, an initial training 2D or 3D representation of a surface of the subject, a subsequent training image of the tumor in the subject and a subsequent training 2D or 3D representation of a surface of the subject. The subsequent training image and the subsequent training 2D or 3D representation are taken at a subsequent point in time than the initial training image and the initial training 2D or 3D representation. The plurality of sets of image data is from a plurality of different subjects.

In another particular embodiment, the computer program 440 comprises instructions, which when executed by a processor 410, cause the processor 410 to determine a subsequent position of a tumor in a subject based on a subsequent 2D or 3D representation of a surface of the subject, an initial 2D or 3D representation of a surface of the subject, an initial image of the tumor in the subject and a CI tumor position determining model trained based on a plurality of sets of image data. Each set of image data comprises an initial training image of a tumor in a subject, an initial training 2D or 3D representation of a surface of the subject, a subsequent training image of the tumor in the subject and a subsequent training 2D or 3D representation of a surface of the subject. The subsequent training image and the subsequent training 2D or 3D representation are taken at a subsequent point in time than the initial training image and the initial training 2D or 3D representation. The plurality of sets of image data is from a plurality of different subjects.

In a further particular embodiment, the computer program 440 comprises instructions, which when executed by a processor 410, cause the processor 410 to update a CI tumor position determining model trained based on a plurality of sets of image data. Each set of image data comprises an initial training image of a tumor in a subject, an initial training 2D or 3D representation of a surface of the subject, a subsequent training image of the tumor in the subject and a subsequent training 2D or 3D representation of a surface of the subject. The subsequent training image and the subsequent training 2D or 3D representation are taken at a subsequent point in time than the initial training image and the initial training 2D or 3D representation. The plurality of sets of image data is from a plurality of different subjects. In such an embodiment, the processor 410 is caused to update the CI tumor position determining model based on at least one set of image data. In an embodiment, each set of image data comprises an initial image of a tumor in a subject, an initial 2D or 3D representation of a surface of the subject, a subsequent image of the tumor in the subject and a subject 2D or 3D representation of a surface of the subject. The subsequent image and the subsequent 2D or 3D representation are taken at a subsequent point in time than the initial image and the initial 2D or 3D representation. In another embodiment, the set of image data used to update the CI tumor position determining model comprises the initial and subsequent 2D or 3D surface representations and difference data representing a difference in tumor position in a subject between a predicted position of the tumor as determined by the CI tumor position determining model and an actual position of the tumor, such as determined using medical imaging of the subject. In a further embodiment, the set of image data comprises the initial and subsequent 2D or 3D surface representations and information of the outcome of a scheduled radiation treatment for the subject.

The proposed technology also provides a computer-readable storage medium 450 comprising the computer program 440. By way of example, the software or computer program 440 may be realized as a computer program product, which is normally carried or stored on a computer-readable medium 450, in particular a non-volatile medium. The computer-readable medium 450 may include one or more removable or non-removable memory devices including, but not limited to a Read-Only Memory (ROM), a Random Access Memory (RAM), a Compact Disc (CD), a Digital Versatile Disc (DVD), a Blu-ray disc, a Universal Serial Bus (USB) memory, a Hard Disk Drive (HDD) storage device, a flash memory, a magnetic tape, or any other conventional memory device. The computer program 440 may, thus, be loaded into the operating memory 420 of the computer for execution by the processor 410 thereof.

Figure 14:
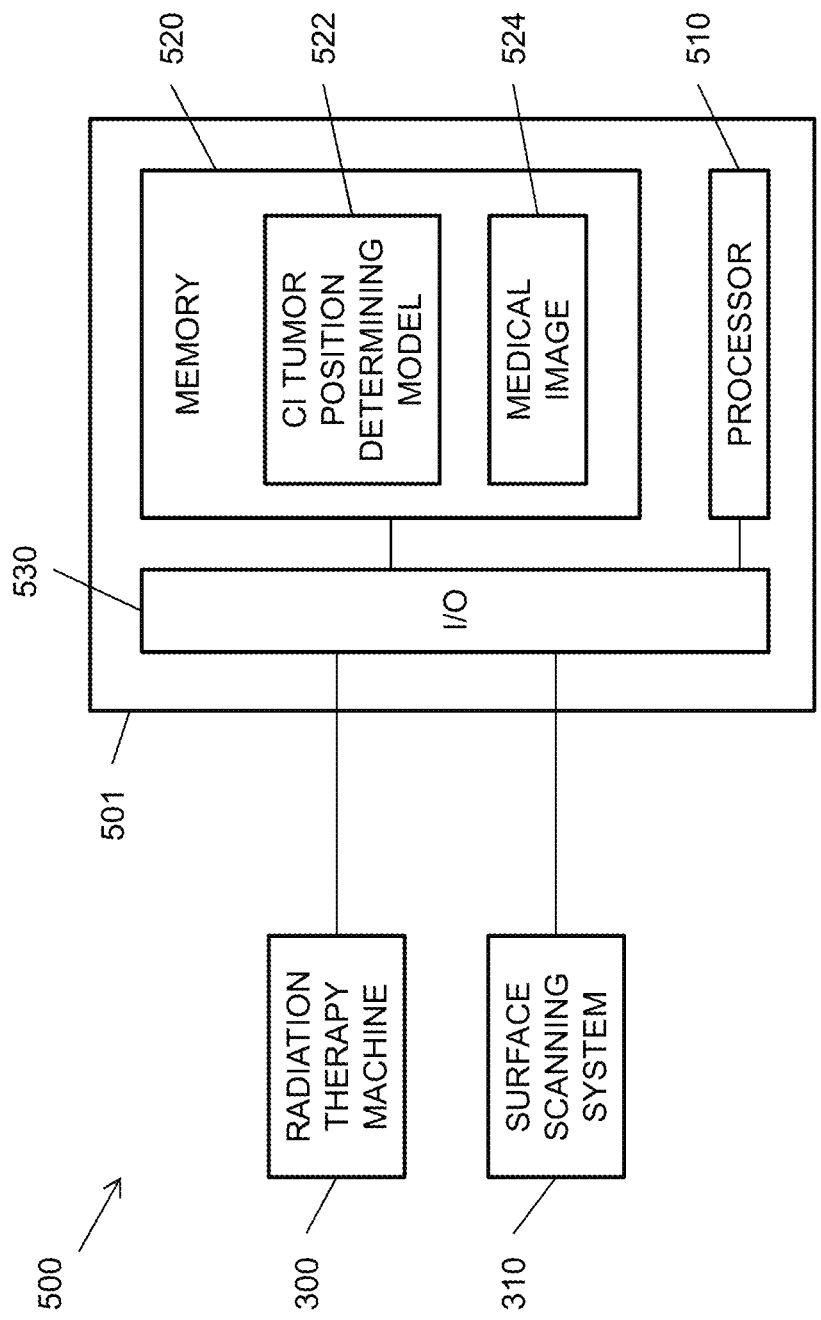
FIG. 14 is a schematic illustration of a radiation therapy system according to an embodiment.

The present invention also relates to a radiation therapy system 500, see FIGS. 11, 12 and 14. The radiation therapy system 500 comprises a radiation therapy machine 300 comprising a radiation source 302 configured to direct a radiation beam into a subject 320 positioned on a couch 304. The radiation therapy system 500 also comprises a surface scanning system 310 comprising a light detector 312 configured to take a surface scan of the subject 320 positioned on the couch 304. The radiation therapy system 500 further comprises at least one memory 520 configured to store a CI tumor position determining model 522 trained based on a plurality of sets of image data. Each set of image data comprises an initial training image of a tumor in a subject, an initial training 2D or 3D representation of a surface of the subject, a subsequent training image of the tumor in the subject and a subsequent training 2D or 3D representation of a surface of the subject. The subsequent training image and the subsequent training 2D or 3D representation are taken at a subsequent point in time than the initial training image and the initial training 2D or 3D representation. The plurality of sets of image data is from a plurality of different subjects. The memory 520 is also configured to store a medical image 524 of the subject 320 positioned on a couch in connection with a radiation therapy simulator. The radiation therapy system 500 additionally comprises at least one processor 510 configured to process the medical image and generate an initial image of a tumor in the subject and an initial 2D or 3D representation of a surface of the subject 320 based on the medical image. The at least one processor 510 is also configured to process the surface scan and generate a subsequent 2D or 3D representation of a surface of the subject 320 based on the surface scan. The at least one processor 510 is further configured to determine a subsequent position of the tumor in the subject 320 based on the subsequent 3D representation, the initial 3D representation, the initial image and the CI tumor position determining model.

In an embodiment, the surface scanning system 310 comprises a light projector 314 in addition to the light detector 312.

The radiation therapy system 500 in accordance with this embodiment is in particular suitable when having access to medical images in its memory 520 that could be used to determine not only the initial tumor images but also the initial 2D or 3D surface representations. For instance, the medical images could be obtained from one or more medical imaging machines, such as CT scanner, CBCT scanner, PET scanner or MRI scanner.

In another embodiment, the radiation therapy system 500 comprises a radiation therapy machine 300 comprising a radiation source 302 configured to direct a radiation beam into a subject 320 positioned on a couch 304. The radiation therapy machine 300 also comprises a first surface scanning system comprising a light detector configured to take an initial surface scan of the subject 320 positioned on a couch in connection with a medical imaging machine 200 and a second surface scanning system 310 comprising a light detector 312 configured to take a subsequent surface scan of the subject 320 positioned on the couch 304 in connection with the radiation therapy machine 304. The radiation therapy system 500 also comprises at least one memory 520 configured to store a CI tumor position determining model 522 trained based on a plurality of sets of image data. Each set of image data comprises an initial training image of a tumor in a subject, an initial training 2D or 3D representation of a surface of the subject, a subsequent training image of the tumor in the subject and a subsequent training 2D or 3D representation of a surface of the subject. The subsequent training image and the subsequent training 2D or 3D representation are taken at a subsequent point in time than the initial training image and the initial training 2D or 3D representation. The plurality of sets of image data is from a plurality of different subjects. The memory 520 is also configured to store an initial image 524 of a tumor in the subject 320 positioned on the couch in connection with the medical imaging machine 200. The radiation therapy system 500 further comprises at least one processor 510 configured to process the initial surface scan and generate an initial 2D or 3D representation of a surface of the subject 320 based on the initial surface scan. The at least one processor 510 is also configured to process the subsequent surface scan and generate a subsequent 2D or 3D representation of a surface of the subject 320 based on the subsequent surface scan. The at least one processor 510 is further configured to determine a subsequent position of the tumor in the subject 320 based on the subsequent 2D or 3D representation, the initial 2D or 3D representation, the initial image and the CI tumor position determining model.

In an embodiment, the first surface scanning system comprises a (first) light projector in addition to the (first) light detector and the second surface scanning system 310 comprises a (second) light projector 314 in addition to the (second) light detector 312.

In this embodiment, a respective surface scanning system is arranged in connection with the radiation therapy machine and the medical imaging machine. This embodiment of the radiation therapy system 500 could therefore be used to handle medical images from which only initial tumor images but not initial 2D or 3D surface representations could be determined.

The memory 520 and the at least one processor 510 may be implemented in a device 501, such as a computer, of the radiation therapy system 500. This device 501 may then be connected, wirelessly or using wires, to the radiation therapy machine 300, the at least one surface scanning system 310 and optionally to the medical imaging machine 200 using an I/O unit 530.

The present invention enables an accurate determination of the position of a tumor in a subject during a radiation therapy session by conducting the determination based on a previously trained CI tumor position determining model, 2D or 3D surface representations and an initial tumor image typically obtained during the treatment planning process. This means that the tumor position can be determined accurately even if the radiation treatment is divided into a plurality of treatment sessions extending over time, such as days or even weeks. The CI tumor position determining model can then accurately determine the position of the tumor in the subject even though the subject's body shape has changed between the treatment sessions, such as for a subject gaining or loosing weight. The CI tumor position determining model may also determine the tumor position for a body deformation due to unintentionally movement of the subject on the couch in connection with the radiation therapy machine and/or due to respiratory movement.

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible. The scope of the present invention is, however, defined by the appended claims.

The invention claimed is:

1. A computer-implemented method of generating a tumor position determining model, the method comprising:
   providing a plurality of sets of image data, each set of image data comprises an initial training image of a tumor in a subject, an initial training two-dimensional (2D) or three-dimensional (3D) representation of a surface of the subject, a subsequent training image of the tumor in the subject and a subsequent training 2D or 3D representation of a surface of the subject, wherein
      the subsequent training image and the subsequent training 2D or 3D representation are taken at a subsequent point in time than the initial training image and the initial training 2D or 3D representation; and
      the plurality of sets of image data is from a plurality of different subjects; and
   training, based on the plurality of sets of image data, a computer-implemented tumor position determining model to determine a subsequent position of a tumor in a subject based on a subsequent 2D or 3D representation of a surface of the subject, an initial image of the tumor in the subject and an initial 2D or 3D representation of a surface of the subject.

2. The method according to claim 1, further comprising:
   determining, for each set of image data, a change in tumor position in a subject based on the initial training image and the subsequent training image; and
   determining, for each set of image data, a change in subject surface based on the initial training 2D or 3D representation and the subsequent training 2D or 3D representation, wherein training the computer-implemented tumor position determining model comprises training the computer-implemented tumor position determining model based on the determined changes in tumor position and the determined changes in subject surface.

3. The method according to claim 1, wherein training the computer-implemented tumor position determining model comprises training, based on the plurality of sets of image data, the computer-implemented tumor position determining model to determine the subsequent position of the tumor in the subject based on a change in subject surface as determined based on the initial 2D or 3D representation of a surface of the subject and the subsequent 2D or 3D representation of a surface of the subject, an initial position of the tumor and tissue type or types in vicinity of the tumor as determined based on the initial image of the tumor in the subject.

4. The method according to claim 1, wherein training the computer-implemented tumor position determining model comprises training, based on the plurality of sets of image data, a computer-implemented tumor position determining machine learning (ML) model to determine a subsequent position of a tumor in a subject based on a subsequent 2D or 3D representation of a surface of the subject, an initial image of the tumor in the subject and an initial 2D or 3D representation of a surface of the subject.

5. The method according to claim 1, wherein
   the initial training 2D or 3D representation of the surface is a 2D or 3D representation of a surface of the subject taken in connection with the initial training image of the tumor in the subject; and
   the subsequent training 2D or 3D representation of the surface is a 2D or 3D representation of a surface of the subject taken in connection with the subsequent training image of the tumor in the subject.

6. The method according to claim 5, wherein the subsequent training image of the tumor in the subject is taken at least multiple days after the initial training image of the tumor in the subject is taken.

7. The method according to claim 1, further comprising:
   providing medical images of subjects; and
   determining, from each medical image of a subject, an initial training image of a tumor in the subject and an initial training 2D or 3D representation of a surface of the subject.

8. The method according to claim 7, wherein the medical images are selected from the group consisting of computed tomography (CT) images, magnetic resonance imaging (MRI) images and positron emission tomography (PET)/CT images.

9. The method according to claim 7, wherein
   providing medical images comprises providing cone beam computed tomography (CBCT) images of subjects; and
   determining the initial training image comprises determining, from each CBCT image of a subject, an initial training image of a tumor in the subject and an initial training 2D or 3D representation of a surface of the subject.

10. The method according to claim 1, wherein the plurality of sets of image data comprises images of tumors in subjects as taken with different image modalities.

11. The method according to claim 9, wherein the different image modalities are selected from the group consisting of computed tomography (CT), positron emission tomography (PET), PET/CT, ultrasound and magnetic resonance imaging (MRI).

12. The method according to claim 1, further comprising:
providing surface scans of subjects taken by a surface scanning system comprising a light detector in connection with taking the subsequent training images; and
determining, from each surface scan, a subsequent 2D or 3D representation of a surface of a subject.

13. A method of determining a position of a tumor in a subject, the method comprising:
providing an initial image of a tumor in a subject and an initial two-dimensional (2D) or three-dimensional (3D) representation of a surface of the subject;
providing a subsequent 2D or 3D representation of a surface of the subject, wherein the subsequent 2D or 3D representation is taken at a subsequent point in time than the initial image and the initial 2D or 3D representation; and
determining a subsequent position of the tumor in the subject based on the subsequent 2D or 3D representation, the initial 2D or 3D representation, the initial image and a computer-implemented tumor position determining model trained based on a plurality of sets of image data, each set of image data comprises an initial training image of a tumor in a subject, an initial training 2D or 3D representation of a surface of the subject, a subsequent training image of the tumor in the subject and a subsequent training 2D or 3D representation of a surface of the subject, wherein
the subsequent training image and the subsequent training 2D or 3D representation are taken at a subsequent point in time than the initial training image and the initial training 2D or 3D representation; and
the plurality of sets of image data is from a plurality of different subjects.

14. The method according to claim 13, further comprising determining a change in subject surface based on the initial 2D or 3D representation and the subsequent 2D or 3D representation, wherein determining the subsequent position of the tumor comprises determining the subsequent position of the tumor in the subject based on the change in subject surface, the initial image and the computer-implemented tumor position determining model.

15. The method according to claim 13, wherein determining the subsequent position of the tumor comprises determining the subsequent position of the tumor in the subject based on a change in subject surface as determined based on the initial 2D or 3D representation and the subsequent 2D or 3D representation, an initial position of the tumor and tissue type or types in vicinity of the tumor as determined based on the initial image and the computer-implemented tumor position determining model.

16. The method according to claim 13, further comprising taking a medical image of the subject, wherein providing the initial image comprises generating the initial image of the tumor in the subject and the initial 3D representation of a surface of the subject based on the medical image.

17. The method according to claim 16, wherein the medical image is selected from the group consisting of a computed tomography (CT) image, a magnetic resonance imaging (MRI) image and a positron emission tomography (PET)/CT image.

18. The method according to claim 16, wherein taking the medical image of the subject comprises taking the medical image of the subject using a medical imaging system arranged at or in connection with a radiation therapy simulator.

19. The method according to claim 13, further comprising taking a surface scan of the subject using a light detector, wherein providing the subsequent 2D or 3D representation comprises generating the subsequent 2D or 3D representation of a surface of the subject based on the surface scan.

20. The method according to claim 19, wherein taking the surface scan comprises taking the surface scan of the subject using the light detector arranged at or in connection with a radiation therapy machine.

21. The method according to claim 13, further comprising calculating a translation vector based on the determined subsequent position of the tumor in the subject and a target position of tumor in the subject.

22. The method according to claim 21, further comprising defining a treatment isocenter based on the determined subsequent position of the tumor in the subject, wherein calculating the translation vector comprises calculating the translation vector based on the defined treatment isocenter and an isocenter of a radiation therapy machine.

23. The method according to claim 21, further comprising repositioning the subject relative to a radiation therapy machine based on the calculated translation vector.

24. The method according to claim 21, further comprising adjusting at least one setting of a radiation therapy machine based on the calculated translation vector.

25. The method according to claim 13, wherein the computer-implemented tumor position determining model is generated according to claim 1.

26. A non-transitory computer-readable medium storing instructions that, when executed by a processor, cause the processor to train, based on a plurality of sets of image data, a computer-implemented tumor position determining model to determine a subsequent position of a tumor in a subject based on a subsequent two-dimensional (2D) or three-dimensional (3D) representation of a surface of the subject, an initial image of the tumor in the subject and an initial 2D or 3D representation of a surface of the subject, wherein each set of image data comprises an initial training image of a tumor in a subject, an initial training 2D or 3D representation of a surface of the subject, a subsequent training image of the tumor in the subject and a subsequent training 2D or 3D representation of a surface of the subject, wherein
the subsequent training image and the subsequent training 2D or 3D representation are taken at a subsequent point in time than the initial training image and the initial training 2D or 3D representation; and
the plurality of sets of image data is from a plurality of different subjects.

27. A non-transitory computer-readable medium storing instructions that, when executed by a processor, cause the processor to determine a subsequent position of a tumor in a subject based on a subsequent two-dimensional (2D) or three-dimensional (3D) representation of a surface of the subject, an initial 2D or 3D representation of a surface of the subject, an initial image of the tumor in the subject and a computer-implemented tumor position determining model trained based on a plurality of sets of image data, each set of image data comprises an initial training image of a tumor in a subject, an initial training 2D or 3D representation of a surface of the subject, a subsequent training image of the tumor in the subject and a subsequent training 2D or 3D representation of a surface of the subject, wherein
the subsequent training image and the subsequent training 2D or 3D representation are taken at a subsequent point in time than the initial training image and the initial training 2D or 3D representation; and
the plurality of sets of image data is from a plurality of different subjects.

28. A radiation therapy system comprising:
a radiation therapy machine comprising a radiation source configured to direct a radiation beam into a subject positioned on a couch;
a surface scanning system comprising a light detector configured to take a surface scan of the subject positioned on the couch;
at least one memory configured to store:
a computer-implemented tumor position determining model trained based on a plurality of sets of image data, each set of image data comprises an initial training image of a tumor in a subject, an initial training two-dimensional (2D) or three-dimensional (3D) representation of a surface of the subject, a subsequent training image of the tumor in the subject and a subsequent training 2D or 3D representation of a surface of the subject, wherein
the subsequent training image and the subsequent training 2D or 3D representation are taken at a subsequent point in time than the initial training image and the initial training 2D or 3D representation; and
the plurality of sets of image data is from a plurality of different subjects; and
a medical image of the subject positioned on a couch in connection with a radiation therapy simulator; and
at least one processor configured to:
process the medical image and generate an initial image of a tumor in the subject and an initial 2D or 3D representation of a surface of the subject based on the medical image;
process the surface scan and generate a subsequent 2D or 3D representation of a surface of the subject based on the surface scan; and
determine a subsequent position of the tumor in the subject based on the subsequent 2D or 3D representation, the initial 2D or 3D representation, the initial image and the computer-implemented tumor position determining model.

29. The radiation therapy system according to claim 28, wherein the surface scanning system comprises a light projector and the light detector.

30. A radiation therapy system comprising:
a radiation therapy machine comprising a radiation source configured to direct a radiation beam into a subject positioned on a couch;
a first surface scanning system comprising a light detector configured to take an initial surface scan of the subject positioned on a couch in connection with a medical imaging machine;
a second surface scanning system comprising light detector configured to take a subsequent surface scan of the subject positioned on the couch in connection with the radiation therapy machine;
at least one memory configured to store:
a computer-implemented tumor position determining model trained based on a plurality of sets of image data, each set of image data comprises an initial training image of a tumor in a subject, an initial training two-dimensional (2D) or three-dimensional (3D) representation of a surface of the subject, a subsequent training image of the tumor in the subject and a subsequent training 2D or 3D representation of a surface of the subject, wherein
the subsequent training image and the subsequent training 2D or 3D representation are taken at a subsequent point in time than the initial training image and the initial training 2D or 3D representation; and
the plurality of sets of image data is from a plurality of different subjects; and
an initial image of a tumor in the subject positioned on the couch in connection with the medical imaging machine; and
at least one processor configured to:
process the initial surface scan and generate an initial 2D or 3D representation of a surface of the subject based on the initial surface scan;
process the subsequent surface scan and generate a subsequent 2D or 3D representation of a surface of the subject based on the subsequent surface scan; and
determine a subsequent position of the tumor in the subject based on the subsequent 2D or 3D representation, the initial 3D representation, the initial image and the computer-implemented tumor position determining model.

31. The radiation therapy system according to claim 30, wherein
the first surface scanning system comprises a light projector and the light detector; and
the second surface scanning system comprises a light projector and the light detector.

* * * * *